United States Patent [19]

Bashaw et al.

[11] 3,944,064
[45] Mar. 16, 1976

[54] SELF-MONITORED DEVICE FOR RELEASING AGENT AT FUNCTIONAL RATE

[75] Inventors: John D. Bashaw, Palo Alto; Alejandro Zaffaroni; Alan S. Michaels, both of Atherton, all of Calif.

[73] Assignee: ALZA Corporation, Palo Alto, Calif.

[22] Filed: Oct. 26, 1973

[21] Appl. No.: 410,244

[52] U.S. Cl. ............... 206/.5; 128/260; 128/214 F; 222/386.5; 206/522; 424/14; 424/19
[51] Int. Cl.² ...................... A23F 1/08; B65D 85/70
[58] Field of Search ....... 206/.5, 522, 437, DIG. 30; 424/15, 19, 14; 128/2 R, 260, 214 F; 222/386.5

[56] References Cited
UNITED STATES PATENTS

| | | | |
|---|---|---|---|
| 3,279,996 | 10/1966 | Long, Jr. et al. | 206/.5 |
| 3,536,040 | 10/1970 | Pickett | 206/.5 |

*Primary Examiner*—William Price
*Assistant Examiner*—Joseph M. Moy
*Attorney, Agent, or Firm*—Paul L. Sabatine; Edward L. Mandell

[57] ABSTRACT

A delivery device for the controlled and continuous release of a useful agent at a functional rate is comprised of an erodible capsule housing a self monitored delivery device attached to a collapsed support. The device is comprised of a hollow container having a wall formed of a self-monitored release rate controlling material permeable to the passage of the agent by diffusion, or the wall is formed of a microporous material whose micropores are a means for holding a self-monitored release rate controlling medium permeable to the passage of the agent by diffusion. The device on its release from the bioerodible capsule in the environment of use releases an effective amount of agent at a functional rate over a prolonged and continuous period of time.

**10 Claims,

SELF-MONITORED DEVICE FOR RELEASING AGENT AT FUNCTIONAL RATE

BACKGROUND OF THE INVENTION

This invention pertains to both a novel and useful delivery device for administering a beneficial agent to produce a local or systemic physiological or pharmacological beneficial effect. The invention resulted from a chronic need for an agent delivery device, particularly gastrointestinal devices, that is easy to use, comfortable to the host, inexpensive and concomitantly can administer an agent at a continuous and controlled rate for a prolonged period of time at a desired functional rate, for example a drug dosage rate. This need existed in the medical, veterinary and pharmaceutical arts because prior attempts to achieve a prolonged release of a useful agent generally has led to unacceptable results. For example, many prolonged release preparations orally administered to achieve a prolonged result used assorted coatings designed to allow the release of the active agent after a certain time in the environment of use, such as in the gastrointestinal tract, led to problems that gave unacceptable results. One problem typically encountered in the gastrointestinal tract, is that in some cases soluble agent diffused through the coatings which often were insoluble in gastric fluids and in other cases some of the coatings resisted disintegration so that prolonged release preparations would pass through the gastrointestinal tract intact. Also, many agent coatings prepared in the past depended on the assumption that the stomach contents were very acid and the intestinal contents were basic to achieve disintegration of these coatings without any real consideration of the physiological variation of pH that can occur for these contents. Therefore, coatings which depended on pH for disintegration were not as efficient as planned and complete drug release was not obtained.

Other prolonged release medication involved the administration of coated particles or pellets, hard capsules and the like to produce a desired concentration of the agent in the environment of use such as the blood, but these two have not led to the desired agent levels. For example, if the dose of the agent gives a repeated administration effect, the concentration in the blood rises to peaks and falls to valleys depending on the number, frequency and availability of the doses. The peak-valley effect may not be satisfactory in terms of providing the best therapy, becuase at the peak, the high concentration may cuase side effects, and in the valley, the concentration may be insufficient to elicit suitable response. Thus, these types of prolonged release preparations, as with other alleged prolonged release preparations, often are not suitable for releasing agent at a controlled rate for a prolonged period of time.

SUMMARY OF THE SPECIFICATION

Accordingly, it is an immediate object of this invention to provide an agent delivery device for the administration of a locally acting or systemically acting agent to produce a physiologic or pharmacologic effect which device essentially overcomes the disadvantages associated with the prior art prolonged release forms of administration.

Still another important object of the invention is to provide a drug device for use in the gastrointestinal tract for releasing drug at a controlled and continuous rate for a prolonged period of time while simultaneously eliminating the necessity for taking drug at repeated intervals.

A further object of this invention is to provide a complete dosage regimen for administering a drug for a particular time period, the use of which requires intervention only for the initiation of the regimen and would also eliminate missed doses because of forgetfulness.

Still a further object of the invention is to provide a drug delivery device for use in the gastrointestinal tract suitable for continuously administering a drug in the stomach and remaining therein until the prescribed dosage regimen is essentially completed before the device is eliminated from the gastrointestinal tract.

Yet still a further object of the invention is to provide an orally administrable drug delivery device for use as a single administration and wherein the device is self-contained and will remain in the stomach for an extended time while administering drug from a drug reservoir by diffusion through a drug release rate controlling material.

Still another object of the invention is to provide a self-monitored device for releasing a useful agent at a functional rate to various environments of use such as body passageways, the vagina, the bladder, streams, rivers, fish ponds and the like.

In attaining the objects, features and advantages of the invention, a novel delivery device is provided for the continuous dispensing of a beneficial agent in the environment of use which device is self-contained, self-activated, operates independently of its surroundings, and can automatically exit from the environment of use after an extended period of drug administration. The delivery device is comprised of a physiologically erodible capsule having an internal space for housing the agent delivery device. The device is comprised of a container that acts as a reservoir for housing an agent. The wall of the container is made of a self-monitored agent homogenous release rate controlling material permeable to the passage of the agent. The wall can also be made of a microporous material containing in its micropores a self-monitored release rate controlling medium permeable to the passage of the agent. The container is fixed to a deformable, hollow support member that can inflate on release of the device from its storage and transport capsule in the environment of use. The support self-deflates after the release of agent to let the device pass from the environment of use. Also, the device can be fabricated of biodegradable materials that biodegrade after a period of time to permit passage of the device from the environment.

Other objects, features and advantages of the invention will be apparent to those skilled in the art from the following detailed description of the invention, taken in conjunction with the drawings and the accompanying claims.

BRIEF DESCRIPTION OF THE DRAWINGS

In the drawings, which are not drawn to scale, but rather are set forth to illustrate various embodiments of the invention, the drawings are as follows.

In the drawings and the specification, like parts in related figures are identified by like numbers. The terms appearing earlier in the specification and in the description of the drawings, as well as various embodiments thereof, are further described in detail elsewhere in the disclosure.

DETAILED DESCRIPTION OF THE DRAWINGS

Figure 1:
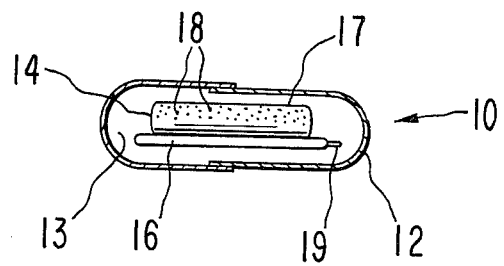
FIG. 1 is a side perspective view of an agent delivery device of the invention housed in a capsule prior to use.

Turning now to the drawings in detail, which drawing are examples of various agent delivery devices of the invention, and which examples are not to be construed as limiting, one generic example of a novel agent delivery device is generally indicated in FIG. 1 by numeral 10. Delivery device 10 is illustrated in side, opened-face perspective view and it is comprised of a bioerodible capsule 12 having an internal space 13 housing an agent delivery device 14. Device 14 is a hollow container 17, also called herein a reservoir container 17, formed of an agent release rate controlling material permeable to the passage of agent 18. Device 14 is suitably fixed to a deformable hollow member 16 that can reversibly expand or collapse on release of device 14 from capsule 12. In FIG. 1, agent delivery device 14 is depicted in miniature in capsule 12 to exemplify one operative embodiment of the invention. An enlarged, detailed illustration of FIG. 1 with other embodiments is set forth in the remaining FIGS. 2 and 6.

Figure 2:
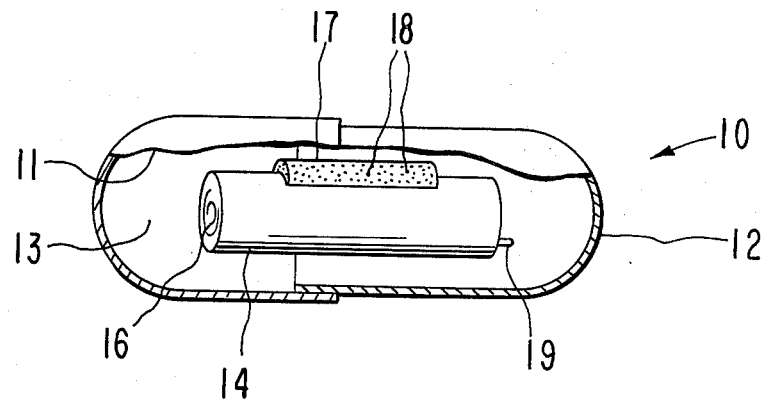
FIG. 2 is an enlarged, side perspective view illustrating an agent delivery device in a closed capsule with a section of the capsule removed for showing a device therein.

Referring to FIG. 2, agent delivery device 10 is illustrated comprised of a bioerodible capsule 12 with a section 11 of capsule 12 removed to illustrate an internal space 13 housing device 14. Capsule 12 is advantageously formed of two parts with one part designed to telescope into the other part for easily housing device 14 in capsule 12. Capsule 12 is made of bioerodible materials, such as gelatin, that, in a biological environment of use, move quickly and easily through the esophagus to the stomach wherein it quickly bioerodes to free device 14. Capsules of other construction and made of other bioerodible materials can also be used for housing the device and for releasing the delivery device 12 in the stomach.

Device 14 in the embodiment of the invention illustrated in FIG. 2, is comprised of a container 17 which functions as a reservoir for containing an agent 18 or a mixture of agents 18. It container 17, consists of substantially a closed container 17 having a wall surrounding and enclosing an internal space that serves as a reservoir for internally storing agent 18. The wall of container 17 is made either of an imperforate agent release rate controlling material permeable to the passage of agent or a microporous material having its micropores filled with a medium permeable to the passage of agent 18. In both embodiments, the permeability is by diffusion. Container 17, is suitably fixed by adhesively joining it to support 16. Container 17 in one embodiment is suitably joined to member 16 with conventional adhesives, such as $\alpha$-cyanoacrylates, acrylic and methacrylic adhesives, epoxies, plasticized polyvinyl adhesives, and the like. Other known techniques, such as thermal joining, casting the support onto the reservoir and the like can be used to fix container reservoir 17 in sealed relationship with member 16. Member 17, in another embodiment, is suitably formed by joining a release rate wall slightly raised above support 16. The wall is joined around its outer edges to define a space that is a reservoir container 17. The space is comprised of the raised inner surface wall and the corresponding wall of support 16. The wall is sealed around all its edges by the above described techniques. In FIG. 2, reservoir container 17 is fabricated by the just described techniques. Member 16 is freely movable from a collapsed state to an expanded state on release of device 14 from capsule 12 and it is returnable to a collapsed position after a period of time. Member 16 contains a gas stored in solid or in liquified form at ambient temperature which as solid or liquid produces at physiologic temperatures a gas that has a vapor pressure in excess of one atmosphere to cause member 16 to inflate to a predetermined size and shape. Member 16 is made of naturally occurring or synthetic flexible polymeric materials that lend themselves to reversible changes in size and shape. Member 16 is equipped with an erodible plug 19 that erodes in the environment of use after a predetermined time to release the gas from member 16 to deflate it to a collapsed state for passage through the lower gastrointestinal tract. In another embodiment, member 16 is made from a material that is permeable to a gas to let the gas slowly diffuse therefrom causing it to deflate for eventual passage through the gastrointestinal tract. In FIG. 2, member 16 is optionally illustrated as a completely sealed tube, but it is to be understood that other embodiments such as envelope, flat bag, balloon and the like are within the mode and manner of the invention.

Figure 3:
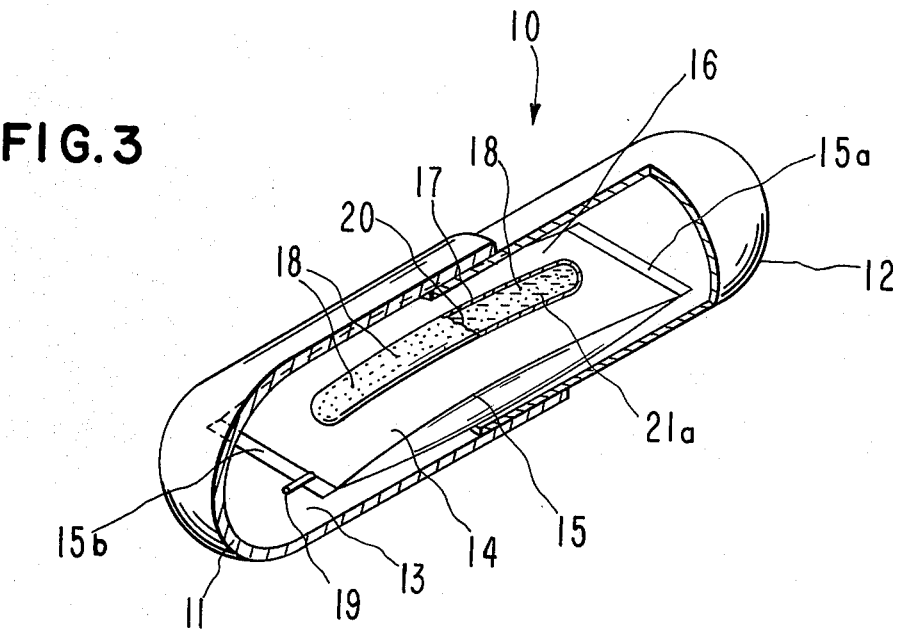
FIG. 3 is a magnified isometric view illustrating another device of the invention confined in a capsule with a central section removed for showing details of the device.

In FIG. 3, another agent delivery device 10 is illustated comprised, in combination, of a swallowable bioerodible capsule 12 made of two telescopically associated non-toxic envelopes with a section 11 of capsule 12 removed to show an internal space 13 carrying an agent delivery device 14. Capsule 12 has a size and shape adapted for oral administration, that is, swallowing and passing by normal paristalsis to the stomachs of humans, farm animals such as cows, horses and the like, household pets such as dogs, and sport animals such as horses. On reaching the stomach, container 12 which is made from gelatin, gelatin derivatives, poly(-vinylalcohol) or the like, quickly and easily disintegrates to release device 14 for discharging a medicament into the stomach.

Device 14 is comprised of a container reservoir 17 for containing an agent 18, or a mixture of agents. Container 17 in FIG. 3 is of tubular shape and it travels all or part of the length of member 16. Container 17 can also embrace other shapes, such as a closed sausage, closed half-circle, triangular and the like. The wall of container 17 can be as previously described, that is, a homogenous wall or a microporous material, with its micropores containing a medium permeable to the passage of drug. Optionally, the medium in the micropores can be gastric fluids which can also serve as a drug release rate controlling medium. Other examples will be presented later in the disclosure.

In FIG. 3, agent 18 is seen at the surface of container 17 after diffusing through the self monitored wall for release from device 10. Container 17 at surface 20 is open to illustrate the interior of container 17. The interior is filled with a carrier 21a, that is a liquid or the like housing agent 18. In operation in the environment of use, agent 18 moves through carrier 21a and then through the wall to the exterior of device 10. Container 17 is suitably joined to deformable member 16 that is made of naturally occurring or synthetic flexible polymeric materials that can readily change size and shape from collapsed to inflated and back to collapsed. Container 17 covers at least a portion of the outer surface of member 16, or it can cover all the surface of member 16. Container 17 is suitably joined to deformable member 16 by adhesive sealing, integral fabrication, heat sealing, multi-layered coating, or other conventional manufacturing means. Deformable member 16 is illustrated in a collapsed position and it is formed of a section of polymeric film material folded in tubular shape and heat sealed together along its longitudinal seams 15. Member 16 contacting opposed surfaces are sealed together along a transverse bottom seam 15a and a transverse top seam 15b to form a completely sealed deformable member. Member 16 can be formed of one or more layers with one or more surfaces of similar or dissimilar films, and it is manufactured with a bioerodible plug 19 that erodes after a period of time to vent the interior of member 16 to its exterior. Member 16 can optionally be formed of a bioerodible material that erodes after a period of time, or it can be formed of a material permeable to a gas that slowly diffuses therethrough to cause an inflated member 16 to collapse. Member 16 contains a gas stored in solid or liquified form at ambient conditions that produces a gas having a vapor pressure in excess of one atmosphere at the termperature of use, that is, in the stomach, to cause member 16 to inflate to a predetermined size and shape. The dimensions of member 16 in the inflated state will of course vary for different animals, but it should be large enough to retain the device in the stomach, that is, slightly larger than the diameter of the pyloric canal which is about 1 cm to 4 cm, usually 2 cm in humans. Hence, in operation, container 12 is administered through the gastrointestinal tract into the stomach where device 14 is freed from capsule 12. Member 16 then inflates to place the container 17 with its release rate controlling wall in position in the stomach to diffuse drug 18 from container 17 at a functional rate throughout the drug administration period. At the end of this period, plug 19 erodes and devices 14 then passes through the lower alimentary tract and out of the body.

Figure 4:
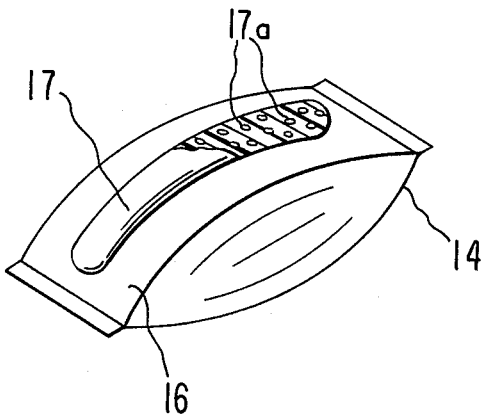
FIG. 4 is the device of FIG. 3 with a section of the delivery means exposed to illustrate the device in operative condition.

FIG. 4 graphically depicts the delivery device of FIG. 3 freed from its container in operative embodiment. In FIG. 4 device 14 is comprised of an inflated tubular member 16 bearing on one of its surfaces a closed reservoir 17 formed of a wall surrounding an enclosed agent containing area, not shown. Reservoir 17 which has an open cross section illustrating micropores 17a in the reservoir 17 material. Reservoir 17 is comprised of a microporous material containing a drug internally housed that can diffuse from the inside of container 17 through micropores 17a at a controlled and continuous rate for a prolonged time to produce a beneficial effect. The size of reservoir 17 will vary to correspond to the size of the host, and it will usually be about 1 mil to 25 mm in diameter and about 1 mil to 50 mm long or larger. Reservoir 17 can be round, cylinderical, cresent, oval, egg, and like container shapes. Reservoir 17 can be integrally formed or made of many parts. Reservoir 17 is made and joined to the supporting structure by conventional techniques, such as casting, lamination, interface sealing, adhesive joining and the like to yield a composite device. Standard manufacture techniques for making the device are well known to the art as described in *Modern Plastic Encyclopedia*, Vol. 46, No. 10A, 1969, and in *ASTM Standards*, Structural Sandwich Constructions, Part 16, T. Peel Test: ASTMD 1876-61, T. Peel Resistance, 1965, published by the American Society for Testing and Materials, and like references.

Figure 5:
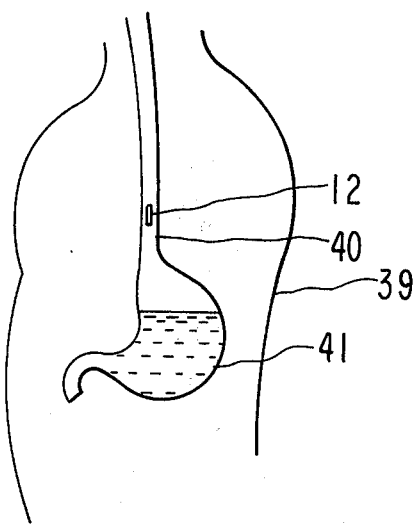
FIG. 5 is a side view diagrammatically illustrating a capsule housing a drug delivery device descending in the esophagus.
Figure 6:
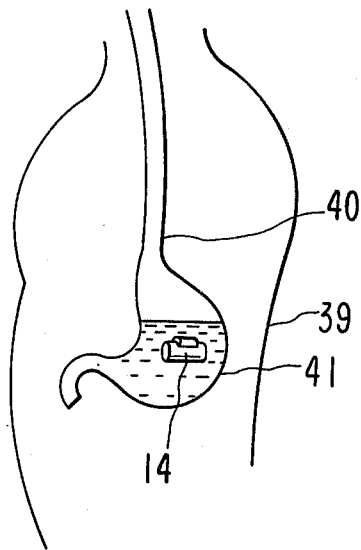
FIG. 6 is a side view diagrammatically depicting a drug delivery device in use in the stomach.

FIG. 5 and FIG. 6 diagrammatically illustrate the use of the agent delivery device of the invention. In FIG. 5 there is seen an outline of a human 39 with a capsule 12 moving through an esophagus 40 toward a stomach 41. In FIG. 6 drug delivery device 14 is seen administering a drug in stomach 41 to produce a prolonged beneficial result.

DETAILS OF THE INVENTION

Delivery device 14 of this invention can be made into different sizes and shapes with these dimensions adapted for administration to a particular animal, reptile and the like, and to the ease of manufacture. The shape of the device is usually tubular but other shapes such as oblong, oblate, prolate, spherical, half-circle, and the like can be used according to the spirit of the invention. Generally, the device is fabricated for oral administration into the stomach and the size of the deformable hollow member 16 of the device in the inflated state will be slightly larger than the diameter of the pyloric canal to keep the device in the stomach during a period of drug release. The size of the pyloric canal of different animals is available in standard medical books, and for humans the size of the inflated member will be about 1 cm in diameter to about 10 cm in length, usually about 2 cm by 4 cm. Other sizes such as 2 cm by 5 cm, 3.14 cm by 5 cm, 4 cm by 4 cm and the like are also within the mode and manner of the invention.

Deformable member 16 bearing closed, hollow reservoir 17 is suitably made from naturally occurring or synthetic materials and it is made of film about 0.2 mils to 100 mils thick, or more; usually 0.4 mils to 20 mils thick, and the like. The walls of member 16 can be made of a single material, a combination of materials in laminated form, elastomeric materials bonded on thin foils, and the like. Illustrative materials suitable for this purpose include silicone, poly(urethanes), poly(acrylonitriles), poly(ethylene), poly(propylene), poly(vinylidene chloride), poly(vinylidene fluoride), acrylic elastomers, ethylene propylene terpolymers, laminates such as poly(ethylene-poly(vinylidene chloride), nylon-poly(vinylidene chloride), poly(ethylene)-poly(vinylidene chloride)-poly(ethylene), poly(ethylene)-poly(vinylalcohol)-poly(vinylidene)chloride, metal foils such as tin foils, aluminum foils, plastic coated foils such as poly(ethylene) coated on tin foil, poly(vinylidene chloride) on tin tin, nylon-poly(vinylidene chloride), acrylic elastomers laminated with foils, and the like.

Exemplary materials for use forming bioerodible plug 19 and also useful for forming deformable membrane 16 when it is optionally made from bioerodible materials, include those materials that bioerode in the environment of use, that is in the stomach, at a predetermined given time, or over a period of time. These materials are those that bioerode by known physiological processes, such as chemical degradation, acidic hydrolysis, enzymatic action, oxidation, reduction, dissolution, slow solubilization and the like biological processes. The bioerosion rate for suitable materials can be easily determined by standard assay procedures that consist of placing a section of bioerodible material in natural or artificial gastric juice at normal body temperature and then observing the rate of erosion over a known period of time. By a prolonged peroid of time for the purpose of this invention is meant 2 hours to 30 days, usually 1 day to 8 days.

Representative bioerodible materials for making the above generally include hydrophilic polymers, uncrosslinked hydroxyalkyl acrylates and methacrylates, hydrolytically biodegradable poly(anhydride) polymers as described in U.S. Pat. Nos. 2,073,799; 2,668,162; and 2,676,945; and in *Introduction to Polymer Chemistry*, Stille, J. K., Chapter 6, 1962 as published by Wiley Publishing Co., bioerodible polyesters as described in *Industrial and Engineering Chemistry*, Vol. 36, No. 3, Pages 223 to 228, 1964; *Macrmol Chem.*, Vol. 75, pages 211 to 214, 1964; U.S. Pat. Nos. 2,703,316; 2,668,162; 3,297,033; and 2,676,945; cross-linked gelatin prepared with a cross-linking agent reactive with the hydroxyl, carboxyl or amino functional groups of the gelatin molecule as described in *J. Polymer Science*, Part A-1, Vol. 5, No. 1, 1967; *J. Polymer Science*, Vol. 54, pages 321 to 335, 1961; *Advances in Protein Chemistry*, Vol. 41, entitled Cross Linkage in Protein Chemistry, 1961, published by Academic Press, Inc.

Other materials that can be used to form bioerodible films and plugs include proteins and hydrocollids of animal and plant origin such as modified collagen, elastin, keratin, fibrin, algin, karaya, pectin, carrageenin, chitin, heparin, locust bean gum, and the like. Also, commercially available synthetic polymers such as poly(ethylene oxide), poly(vinylpyrrolidone), poly(ethyleneimine), poly(acrylic acid) copolymers of acrylamide and methacrylamide up to 40% by weight of N-methylene bisacrylamide or N,N-dimethyl urea, water soluble polyurethanes, and the like.

Exemplary materials suitable for inflating deformable member 16 are inorganic and organic compounds that are essentially solid or liquid at ambient temperature, usually at 20° to 35° C, while at physiological temperatures, for example 35° to 40° C, they freely change to a gas whose vapor phase is in equilibrium with its solid or liquid phase to exert a vapor pressure in excess of one atmosphere. Typical compounds are those compounds with a boiling point, BP, as follows: halogenated hydrocarbons, fluorochlorinated lower saturated aliphatic hydrocarbons, halogenated lower alkanes of 1 to 4 carbon atoms and the like, such as diethyl ether BP 34.6° C, methyl formate BP 31.5° C, tetramethyl silane BP 26.5° C, iso-pentane BP 27.9° C, perfluoropentane isomers BP 31.0° C, n-pentane BP 36° C, diethenyl ether BP 28° C and the like. Usually the amount of gas stored in the liquified phase in deformable member 16 will be about 0.1 cc to 10,000 cc or higher, usually about 0.2 cc to 0.5 cc, and the volume of the vapor phase will be from 1 percent to 50 percent of the inflated member.

Representative of drug release rate controlling materials useful for forming the reservoir of the device, that is the container, and having a drug contained therein, are materials that are permeable to the drug to permit passage of the drug by diffusion from within the container through the material that is essentially imperforate or homogenous at predetermined rates. In this process, the drug dissolves and equilibrates in the material, and then diffuses in the direction of lower chemical potential, that is, toward the reservoir's surface. The rate of passage of the drug through the material is described by Fick's Law of Diffusion and it is generally dependent, in the case of diffusion, on the solubility of the agent therein, as well as on the thickness of the material. This means that selection of appropriate materials for fabricating the reservoir will be dependent on the particular drug to be used. By varying the composition and thickness of the reservoir, the dosage rates per area of the gastrointestinal device can be controlled for this material acts to meter the diffusion of the drug from the reservoir.

In drug delivery devices of the invention having a reservoir formed from a microporous material, that is, a container formed of this material that contains drug internally disposed therein, is released form the device by diffusion through the micropores that contain in the micropores a medium that is permeable to the drug at a controlled and predetermined rate. That is, in this material, the rate of passage or the rate of drug release from the hollow reservoir is governed by diffusion of the drug through the micropores, or the microholes of the material forming the reservoir. When a medium is present in the micropores it can consist, in one embodiment, of a liquid phase comprised of a solution, a colloidal solution, a suspension, or a sol, and the solution can be polar, semi-polar or non-polar; or it can be gastric fluid absorbed by the reservoir from the stomach. In these media, the active drug can have different degrees of solubility, such as fully soluble, partially soluble and the like, to act in cooperation with the reservoir material for achieving a controlled release rate.

The materials suitable for fabricating the walls of the reservoir of the drug device are generally those materials capable of forming walls, with or without micropores, through which the drug can pass at a controlled rate of release by diffusion. Such materials are referred to in this specification and the appended claims as "release rate controlling materials" or "self-monitored materials." Suitable materials for forming the wall are naturally occurring or synthetic materials, preferably materials that are biologically compatible with body fluids, the gastrointestinal tract tissues, the vagina, in vivo passageways, and the like and they are capable of medical use of prolonged periods of time.

Exemplary naturally occurring or synthetic materials suitable for fabricating the reservoir's walls are release rate controlling materials such as poly(methylmethacrylate), poly(butylmethacrylate), plasticized poly(vinylchloride), plasticized nylon, plasticized solft nylon, plasticized poly(ethylene terephthalate), natural rubber, poly(isoprene), poly(isobutylene), poly(butadiene), poly(ethylene), poly(tetrafluoroethylene), poly(vinylidene chloride), poly(acrylonitrile), cross-linked poly(vinylpyrrolidone), poly(trifluorochloroethylene), chlorinated poly(ethylene), poly(4,4'-isopropylidene diphenylene carbonate), and the like. Also, by way of nonlimiting example, copolymers such as vinvlidene chloride acrylonitrile, vinyl chloride diethyl fumarate and the like. Examples of other materials include silicone rubbers, especially the medical grade poly(dimethylsiloxanes), ethylene propylene rubber, and silicone-carbonate copolymers, copolymers of styrene and butadiene, modified insoluble collagen, cross-linked insoluble poly(vinylalcohol), cross-linked partially hydrolyzed insoluble poly(vinylacetate), and surface treated silicone rubbers as described in U.S. Pat. No. 3,350,216. Other polymeric membranes that are biologically compartible and do not adversely affect the drugs can be used.

Additionally, other materials permeable to the passage of deliverable agents that are suitable for the present purpose include copolymers such as acrylonitrile dithioglycidol, acrylonitrile ethylene oxide, poly(vinyl butyral) comprised of 11% to 45 percent free hydroxyls, anisotropic permeable microporous membranes of ionically associated polyelectrolytes, the microporous polymers formed by the coprecipitation of a polycation and a polyanion as described in U.S. Pat. Nos. 3,276,589; 3,541,005; 3,541,006; 3,546,142, and the like; treated aliphatic polyamide membranes as in U.S. Pat. Nos. 2,071,253; 2,966,700; 2,999,286, and the like; vinylidene chloride vinyl chloride copolymer 40/60 and 10/90; ethylene vinylacetate acrylate; vinyl chloride acrylonitrile copolymer 80/20, 75/25, 50/50 and the like; vinylidene chloride acrylonitrile copolymer 60/40 and 12/88; water insoluble natural gums, and the like. Also, microporous materials such as cellulose diacetate, cellulose triacetate, poly(urethanes), poly(arylenes), poly(carbonates) and the like. For example, the wall can comprise insoluble, nonerodible cellulose, acylated cellulose, esterified celluloses, cellulose acetate propionate, cellulose acetate butyrate, cellulose acetate phthalate, cellulose acetate diethylaminoacetate, poly(electrolytes) with a pore size of 7 to 50A, epoxy resins, poly(olefins), poly(vinylchlorides) with a pore size of about 50A or less to 150 microns or larger as conventionally made by leaching out incorporated salts, soap micelles, starch or the like materials to give a microporous membrane. Also, the materials that can be used include those materials having homogenous properties and microporous properties, such as cross-linked gelatinous membranes; and the like. The rate controlling structures formed from the materials can be isotropic, wherein the structure is homogenous throughout the cross-section of the wall, or it can be anisotropic wherein the structure is non-homogenous. The rate controlling structures are commerically available and they can also be made by different art known methods, for example, etched nuclear track, leaching, polyelectrolytic processes, ion exchange polymer reactions, and by other techniques as described in *Synthetic Polymer Membranes*, by R. E. Kesting, Chapters 4 and 5, 1971, published by McGraw Hill, Inc., and in *Ultrafiltration, Chemical Reviews*, Vol. 18, pages 373 to 455, 1934. Generally, materials possessing from 5 to 95 percent pores and having an effective pore size of from about 10 angstroms to about 100 microns can be suitably employed as microporous walls in the practice of this invention.

The rate of release of agent or drug, that is, the permeability, through various diffusive medium in the micropores of the reservoir wall can be easily determined by those skilled in the art by standard procedures, as described in *Encyl. Polymer Science and Technology*, Vol. 5 and 9, pages 65 to 82 and 794 to 807, 1968; and the references cited therein, in *Membrane Science and Technology*, by Flinn, James E., pages 16 to 32, and 120 to 138, 1970 published by Plenum Press Inc., *Chemical Engineers Handbook*, pages 17–42 to 17–45, 1963 published by McGraw Hill, Inc. One applicable method employs Fick's Law of Diffusion, wherein the flux of drug through a convection-free medium, for example, a liquid present in a porous membrane is given by the equation:

$$J = \frac{\epsilon D}{\tau} \frac{dc}{dx}$$

wherein
$J$ is the flux in gm/cm$^2$sec.,
$\epsilon$ is the porosity in cm$^3$/cm$^3$,
$\tau$ is the tortuosity factor,
$D$ is the diffujsion coefficient cm$^2$/sec,
$dc/dx$ is the drug concentration gradient across the barrier.

Thus, when the diffusion coefficient is assumed to be independent of concentration, and the concentration at the outside surface is negligibly small, the equation can be expressed as follows:

$$J = \frac{\epsilon D}{\tau} \frac{C_s}{l}$$

wherein
$C_s$ is the saturation solubility of the drug in the diffusive medium, and
$l$ is the barrier thickness.

The diffusion coefficient D will be in the order of 2 × 10$^{-6}$ cm$^2$sec$^{-1}$ when the drug has a small nolecular diameter, for example, about 10A and the pore diameter of the microporous wall is large in comparison with the molecular drug diameter, for example, at least greater by a factor of 10. However, when the pore diameter of the rate controlling membrane is reduced relative to that of the molecular drug diameter, to for example from 10 to about three times the molecular diameter, the diffusion coefficient D will decrease to values as low as 2 × 10$^{-8}$ cm$^2$sec$^{-1}$. When the ratio of membrane pore diameter to molecular drug diameter significantly is below about 3, the membranes are considered to be homogeneous diffusion materials. Thus, by varying pore diameter or porosity of the microporous wall materials, substantial changes in drug release rate wall can be brought about while still using the same wall materials.

The rate of release of a drug through various homogeneous reservoir wall materials can easily be determined by those skilled in the art by standard procedures. In this manner, particular imperforate wall materials used as the reservoir for the drug release rate controlling barrier for release of drug from the hollow reservoirs can be selected. Various techniques, such as the transmission method, the sorption-desorption method, and the like, can be used to measure the permeability. One technique that has been found to be eminently well suited is to cast or hot press a film of the material to a thickness in the range of 2 to 60 mils. The film is used as a barrier between a rapidly stirred (i.g., 150 r.p.m.) saturated solution of the drug and a rapidly stirred solvent bath, both maintained at constant temperature (typically 37° C). Samples are periodically withdrawn from the solvent bath and analyzed for drug concentration. By plotting the drug's concentration in the solvent bath versus time, the permeability constant P of the material is determined by the Fick's First Law of Diffusion.

$$\text{Slope of plot} = \frac{Q_1 - Q_2}{t_1 - t_2} = P \frac{AC}{h}$$

wherein
- $Q_1$ = cumulative amount of drug in solvent in micrograms at $t_1$
- $Q_2$ = cumulative amount of drug in solvent in micrograms at $t_2$
- $t_1$ = elapsed time to first sample, i.e., $Q_1$
- $t_2$ = elapsed time to second sample, i.e., $Q_2$
- $A$ = area of membrane in cm$^2$
- $C$ = initial concentration of drug
- $h$ = thickness of membrane in cm. By determining the slope of the plot, i.e., $$\frac{Q_1 - Q_2}{t_1 - t_2},$$

and solving the equation using the known or measured values of A, C, and h, the permeability P constant in cm$^2$/time of the material for a given drug is readily determined. The rate of drug release through different drug release rate controlling wall materials can be easily determined by those skilled in the art by standard procedures, as described in *Encyl. Polymer Science and Technology*, Vols. 5 and 9, pages 65 to 82 and 794 to 807, 1968; and the references cited therein; in *J. Pharm. Sci.*, Vol. 52, pages 1145 to 1149, 1963; ibid., Vol. 53, pages 798 to 802, 1964; ibid., Vol. 54, pages 1459 to 1464, 1956; ibid., Vol. 55, pages 840 to 843 and 1224 to 1239, 1966; the references cited therein, and the like.

The solubility of a drug in a diffusive medium used in the micropores can be determined by various art known techniques. One method consists in preparing a solution of the given drug and ascertaining by analysis the amount of drug present in a definite quantity of the medium. A simple apparatus for this purpose consists of a test tube of medium size fastened upright in a water bath maintained at constant temperature. The medium and drug are placed in the tube and stirred by means of a motor driven rotating glass spiral. After a given period of stirring, a definite weight of the medium is analyzed and the stirring continued for an additional period of time. If the analysis shows no increase of dissolved substance after the second period of stirring, the results are taken as the degree of solubility of the drug in the medium. Numerous other methods are available for the determination of the degree of solubility of a drug in a liquid medium. Typical methods used for the measurement of solubility are chemical analysis, measurement of density, refractive index, electrical conductivity, and the like. Details of various methods for determining solubilities are described in *United States Public Health Service Bulletin No. 67* of the Hygienic Laboratory; *Encyclopedia of Science and Technology*, Vol. 12, pages 542 to 556, 1971, McGraw Hill, Inc.; *Encyclopaedic Dictionary of Physics*, Vol. 6, pages 545 to 557, 1962, Pergamon Press, Inc.; and the like.

The diffusion coefficient of a drug is broadly determined by measuring the rate a drug transfers from one chamber through a sintered glass filter of known pore size and thickness into another chamber and calculating from the obtained data the drug transfer rate. The method when used for a diffusive medium is carried out by adding to a first conical flask equipped with a ground glass stopper and a stirring bar, a measured amount of medium and simultaneously, the drug in the same medium is added to a second conical flask while keeping the level of the medium in the two flasks the same. Next, the flasks are stirred, the samples drawn at various time intervals for analysis. The measured rate of drug transport through the sintered glass filter, and the concentration difference of the drug in the two flasks is then calculated. These procedures are known to the art in *Proc. Roy. Sci. London*, Ser. A, Vol. 148, page 1935; *J. Pharm. Sci.*, Vol. 55, pages 1224 to 1229, 1966, and references cited therein. The diffusion coefficient of a drug in the solid carrier can also be experimentally determined by using the above apparatus or similar apparatus and procedures as described in *Diffusion in Solids, Liquids and Gasses*, by Jost, W., Chapter XI, pages 436 to 488, 1960, Revised Edition, Academic Press, Inc., New York.

The solubility of the agent in the release rate controlling material comprising the homogeneous wall of the gastrointestinal device broadly is determined by preparing a saturated solution of a given agent and ascertaining, by analysis, the amount present in a definite area of the material. For example, the solubility of the agent in the homogeneous wall is determined by first equilibrating the wall material with a measured saturated solution of the agent at a known temperature and pressure, for example 37° C and one atmosphere. Next, agent is desorbed from the saturated homogeneous wall material with a suitable solvent for the agent. The resultant solution for the agent then is analyzed by standard techniques such as ultraviolet, visible spectrophotometry, refractive index, polarography, electrical conductivity and the like, and calculating from the data the concentration, or solubility of the agent in the material.

The active drugs that can be administered with the gastrointestinal delivery device of the invention, is administered in accordance with their known use and dose, and combinations of these drugs can also be administered, as described in the *Pharmacological Basis of Therapeutics*, 14th Edition, Goodman, L. S., and Gilman, A., 1970, The Macmillan Co.; *Physicians' Desk Reference*, 25th Edition, 1971, Medical Economics, Inc.; and *Remington's Pharmaceutical Sciences*, 14th Edition, 1970, Mack Publishing Co.; include without limitation for example, drugs acting on the central nervous system such as hypnotics and sedatives such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and $\alpha$-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxazid, nialamide, phenelzine, imipramine, tranylcypromine, pargylene and the like; tranquilizers such as chloropromazine, promazine, fluphenazine reserpine, deserpidine, meprobamate, benzodiazepines such as chlordiazepoxide, and the like; anticonvulsants such as primidone, diphenylhydantoin, ethotoin, pheneturide, ethosuximide and the like; muscle relaxants and anti-parkinson agents such as mephenesin, methocarbomal, trihexylphenidyl, biperiden, levo-dopa, also known as L-dopa and L-$\beta$-3-4-dihydroxyphenylalanine, and the like; analgesics such as morphine, codeine, meperidine, nalorphine and the like; antipyretics and anti-inflammatory agents such as aspirin, salicylamide, sodium salicylamide and the like; local anesthetics such as procaine, lidocaine, naepaine, piperocaine, tetracaine, dibucaine and the like; antispasmodics and anti-ulcer agents such as atropine, scopolamine, methscopolamine, oxyphenonium, papaverine, prostaglandins such as $PGE_1$, $PGE_2$, $PGF_{1\alpha}$, $PGF_{2\alpha}$, PGA and the like; anti-microbials such as penicillin, tetracycline, oxytetracycline, chlorotetracycline, chloramphenicol, sulfonamides and the like; antimalarials such as 4-aminoquinolines, 8-aminoquinolines and pyrimethamine; hormonal agents such as prednisolone, cortisone, cortisol and triamcinolone; androgenic steroids, for example, ethyltestosterone, fluoximesterone and the like; estrogenic uterine contraceptive steroids, for example, $17\beta$-estradiol and ethinyl estradiol; progestational uterine contraceptive steroids, for example, $17\alpha$-hydroxyprogesterone acetate, 19-norprogesterone, nor-ethindrone and the like; sympathomimetic drugs such as epinephrine, amphetamine, ephedrine, norepinephrine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; antiparasitic agents such as bephenium hydroxynaphthoate and dichlorophen, dapsone and the liek; neoplastic agents such as mechlorethamine, uracil mustard, 5-fluorouracil, 6-thioguanine, procarbazine and the like; hypoglycemic drugs such as sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents. Also, the drugs can be present as the pharmacologically accpetable derivatives, such as ethers, salts, molecular complexes, esters, amides, acetals, etc., that lend themselves to passage into the circulatory system. These derivatives can be prepared by art known techniques and then used in the practice of the invention. Of course, the drug derivative should be such as to convert to the active drug within the body through the action of body enzymes assisted transformation, pH, specific organ activities, and the like. Of course, the container 17 can also house other agents, such as insecticides, mineralized fertilizers, organic fertilizers, chemical reaction products, and the like. That is, the expression agent includes matter beneficial to man, animals, reptiles, avians and the like.

The amount of active agent incorporated in the reservoir varies depending on the particular agent, the desired effect, and the time span over which it is desired to release the agent. Since devices of different sizes and shapes are intended to provide complete dosage regimen, there is no critical upper limit on the amount of agent incorporated in the device. The lower limit will depend on the activity of the agent and the time span of its release from the device. In general, therefore, the amount of, for example, drug incorporated in the device is non-limited and it is an amount equal to, or larger than, the amount of drug that on release from the device that is effective for bringing about the drug's physiological or pharmacological local or systemic effects. For example, the amount of drug present in the delivery device when the device is used for adult humans for a period of time of four to six days to achieve local or systemic effect is for various drugs, such as propantheline 120 to 300 mg in the device; for glutamic acid hydrochloride an amount in the device of 2400 to 3000 mg; for pargyline hydrochloride 50 to 100 mg; for erythrityl tetranitrate 50 to 100 mg; mannitol hexanitrate 75 to 100 mg; ephedrine sulfate 400 to 600 mg; nylidrin hydrochloride 12 to 48 mg; bethanechol chloride 120 to 480 mg; phentolamine 100 to 400 mg; guanethidine 100 to 1000 mg; enitabas 3 to 25 mg; atropine 100 mcg to 1250 mcg; and the like.

Agent delivery reservoir 17 used according to the invention can be prepared by standard manufacturing procedures. For example, an agent in solid, liquid, sol, emulsion or like form is either in presently usable form or it is mixed with a carrier that can be a monomer, a polymerizable copolymer, a prepolymer in solid, liquid or like form. The agent is distributed therethrough by ball milling, calendering stirring or like procedure. Next, the agent is fed into a container that is made by standard manufacturing techniques such as molding, casting, extruding, drawing or the like, depending on the polymeric material. Finally, the container is coated, laminated, glued, heat joined or the like onto a deformable hollow member. Alternative procedures for preparing the container filled with an agent such as solution saturating a hollow polymer container with an agent by immersion, polymerizing monomers around an agent, can also be used. Other standard manufacturing procedures are described in *Modern Plastic Encyclopedia*, Vol. 46, pages 62 to 70, 1969, and those well known to those skilled in the art can be used herein.

A typical example will serve to illustrate the invention without being limiting thereof. To 25 parts by weight of progesterone is added 70 parts by weight of silicone oil and the mixture stirred to a uniform consistency. Next, 0.25 parts by weight of stannous octoate catalyst is added and the mixture cast into a rectangular mold 6 mm × 6 mm × 60 mm, and the polymer allowed to cure for 30 minutes at ambient conditions to yield a drug reservoir. After curing, the reservoir is inserted into a polyethylene hollow container and one end thereof sealingly closed with a nylon plug. The other end is similarly closed. The filled container is then sealingly joined with standard epoxy adhesives to a collapsed, closed tubular balloon containing 0.5 ml of diethyl ether to yield a drug delivery device mounted to a support. The device is placed in a gelatin capsule, and it will release about 4.3 micrograms of progesterone per day.

Another drug delivery device is fabricated as follows: first, a container of tubular configuration comprised of a very thin sheet of polymeric silicon is sealed together along its contacting peripheries. Then, one end is closed to define an inner agent housing area. After filling through the open end with any suitable agent such as a crystalline sympathomimetic anine, the open end is sealed to form a closed container. The container is then adhesively bonded to a laminated, flexible resilient closed support along one surface thereof. The self monitored fully integrated device is then placed into one end of a capsule and the other end pushed over it to close the capsule. This device, as made according to the spirit of the invention, is ready for use to give a beneficial effect in an in vivo environment.

Another example representative of the spirit of the invention is as follows: an elipsoidal collapsable balloon with minor and major axes of 3 cm and 5 cm is fabricated from a copolymer of poly(vinylidene chloride) and poly(vinyl chloride) by conventional vacuum forming and heat sealing process. Before the final heat seal is made, 0.5 cm$^3$ of diethyl ether is metered into the balloon. Passing through the heat seal is a slowly water soluble filament 0.3 cm in length with a diameter of 0.03 cm which consists of a slowly water soluble copolymer of poly(vinyl alcohol) and poly(ethylene). The ratio of vinyl alcohol units to ethylene units is 6:1.

Affixed to the exterior of the expandable collapsable balloon is a poly(ethylene) film 0.03 cm thick with an area of 10 cm$^2$, with the film covering only a portion of the balloon. The film is secured at its edges to the balloon to provide a hollow space between the film and the balloon. The space between the poly(ethylene) film and the collapsable balloon contains 1 mg of norgestrel, a contraceptive agent, suspended in 0.2 cm$^3$ of sesame oil.

At room temperature, the assembly previously described can be housed within a No. 000 gelatin capsule. However, upon ingestion of the capsule and its subsequent rapid dissolution in the stomach, the collapsable balloon rapidly expands to the dimensions previously given as the ether vaporizes at physiologic temperatures. This keeps the total delivery system in the stomach during the drug delivery period. Drug is delivered by diffusion through the poly(ethylene) film at a contraceptive dose of 0.05 mg/day of the active agent, norgestrel.

Throughout the lifetime of the system, the filament of poly(vinyl alcohol) poly(ethylene) copolymer as previously described has been uniformly dissolving in the gastric fluids. A programmed, total dissolution will occur after 20 to 22 days. This results in complete collapse of the balloon and subsequent elimination from the gastrointestinal tract. The system just described represents a "once a month" application of oral contraception.

Among the advantages of the device of the invention are the ease of construction by standard manufacturing techniques devices into units of different sizes, especially of a miniaturized size, also of shapes and forms that are suitable for delivering a drug internally to an animal or human. Another important advantage of the claimed delivery device is its ability to dispense at a controlled rate, a beneficial agent having a wide variety of chemical and physical properties and over a wide range of release rates. Also, the device is adapted for other body openings and passages such as the bladder, vagina and the like. Still another important advantage of the invention resides in the device's ability to effectively control the rate of release of the drug from the device throughout the major portion of drug administration in a substantial zero order release rate. A further advantage of the device resides in the use of low cost substantially vapor and fluid impermeable materials for the power communicating element resulting in a unit suitable for disposal, after comparatively short periods of use, for example, a day or week, without undue economic hardship on the user, yet providing a continuous and controlled administration of drug without any external energy source. Additionally, the device can be used to release active agents in rivers, streams and other environments of use. And, though the invention has been described in detail, it will be understood that certain changes and modifications can be made without departing from the spirit and scope of the invention.

We claim:

1. A device for the controlled and continuous release of a useful agent to an environment of use wherein the device is comprised of a container having a wall enclosing a hollow area, a reservoir formed by the container wall's inner surface as a means for storing the agent, the container wall additionally formed in at least a part of a self-monitored release rate controlling essentially imperforate homogenous material permeable to the passage of the agent by diffusion for releasing agent from the reservoir, a support member for carrying the container with the wall of the container covering at least a portion of the surface of the support and suitably fixed thereto, said support member movable from a collapsed position to an expanded position and movable from an expanded position to a collapsed position after a period of agent release time, and wherein agent is metered from the reservoir through the wall in a useful amount for a prolonged period of time when the device is in the selected environment of use.

2. A device for the controlled and continuous release of a useful agent according to claim 1 wherein a part of the wall of the container is a part of the support member.

3. A useful device for the release of a useful agent, wherein the device is comprised of a container having a wall enclosing a hollow area, a reservoir formed by the container wall's inner surface as a means for storing the agent, said container wall defining the reservoir formed in at least a part of a microporous material whose micropores contain an agent release rate controlling medium permeable to the passage of the agent at a predetermined rate by diffusion, a support member for carrying the container with a wall of the container covering at least a portion of the support and suitably united thereto, with the support member movable from a collapsed position to an expanded position and returnable to a collapsed position after a period of agent release time, and wherein agent is metered from the reservoir by passage through a medium housed in the micropores of the wall of the container in an effective amount for a prolonged period of time when the device is placed in the environment of use.

4. A device for the controlled and continuous release of a useful agent according to claim 3 wherein a part of the wall of the container is a part of the support member.

5. A delivery device for the controlled and continuous release of a beneficial agent, the device comprising in combination,
   a. a bioerodible capsule providing an internal space therein,
   b. a delivery device housed in the capsules, the device comprising,
   c. a container with an internal space for containing a beneficial agent, said container having a wall formed of a release rate controlling imperforate polymeric material permeable to the passage of the agent by diffusion, or a wall of microporous material whose micropores are a means for containing a liquid release rate controlling medium permeable to the passage of the agent by diffusion,
   d. a reservoir defined by the container's internal space as means for containing beneficial agent that is released from the device by passage through the release rate controlling wall or through a release rate controlling medium in the micropores of the microporous material, the container joined to,
   e. a hollow deformable closed support member, said member movable from a collapsed position to an expanded position on release of the device from the capsule and movable from an expanded position to a collapsed position after a period of time,
f. and wherein agent is metered from the container through the wall in a therapeutically effective amount for a prolonged period of time on release of the device from the capsule in the environment of use.

6. A delivery device for the controlled and continuous release of agent according to claim 5 where the hollow deformable member is provided with a bioerodible plug that on bioerosion in a physiologic environment vents the interior of the member to its exterior.

7. A delivery device for the controlled and continuous release of agent according to claim 5 wherein the hollow deformable member is formed of an elastic material permeable to a gas that slowly diffuses through the material to move the member from an expanded position to a collapsed position.

8. A delivery device for the controlled and continuous release of agent according to claim 5 wherein the hollow deformable member contains a liquid means for producing a gas that has a vapor pressure above one atmosphere or physiological temperature.

9. A delivery device for the controlled and continuous release of an agent according to claim 5 wherein the container contains an agent that produces a local or systemic effect on its release from the container by diffusion in a biological environment.

10. A delivery device for the controlled and continuous administration of an agent according to claim 5 wherein the hollow deformable member is formed of a material that bioerodes at a physiological temperature in the physiological environment.

* * * * *